(12) United States Patent
Qin et al.

(10) Patent No.: US 6,939,914 B2
(45) Date of Patent: Sep. 6, 2005

(54) HIGH STIFFNESS ABSORBENT POLYMERS HAVING IMPROVED ABSORBENCY RATES AND METHOD FOR MAKING THE SAME

(75) Inventors: Jian Qin, Appleton, WI (US); Richard Norris Dodge, II, Appleton, WI (US); Sridhar Ranganathan, Suwanee, GA (US); Cathleen M. Uttecht, Menasha, WI (US); Xiaomin Zhang, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 167 days.

(21) Appl. No.: 10/291,237

(22) Filed: Nov. 8, 2002

(65) Prior Publication Data

US 2004/0092658 A1 May 13, 2004

(51) Int. Cl.[7] ................................................. C08F 2/16

(52) U.S. Cl. ..................... 524/800; 604/358; 604/372; 525/329.5; 526/318.3; 526/323; 526/326; 526/330

(58) Field of Search ..................... 524/800; 604/358, 604/372, 368; 525/329.5; 526/318.3, 323, 326, 330

(56) References Cited

U.S. PATENT DOCUMENTS

| | | |
|---|---|---|
| 4,127,547 A | 11/1978 | Smarook |
| 4,179,540 A | 12/1979 | Smarook |
| 4,394,930 A | 7/1983 | Korpman |
| 4,410,571 A | 10/1983 | Korpman |
| 4,559,243 A | 12/1985 | Pässler et al. |
| 4,758,466 A | 7/1988 | Dabi et al. |
| 5,149,335 A | 9/1992 | Kellenberger et al. |
| 5,252,619 A | 10/1993 | Brownscombe et al. |
| 5,268,224 A | 12/1993 | DesMarais et al. |
| 5,290,820 A | 3/1994 | Brownscombe et al. |
| 5,300,054 A | 4/1994 | Feist et al. |
| 5,304,161 A | 4/1994 | Noel et al. |
| 5,328,935 A | 7/1994 | Van Phan et al. |
| 5,334,621 A | 8/1994 | Beshouri |
| 5,338,766 A | 8/1994 | Phan et al. |
| 5,358,974 A | 10/1994 | Brownscombe et al. |
| 5,364,382 A | 11/1994 | Latimer et al. |
| 5,439,458 A | 8/1995 | Noel et al. |
| 5,447,727 A * | 9/1995 | Graham ..................... 424/487 |
| 5,490,846 A | 2/1996 | Ellis et al. |
| 5,509,915 A | 4/1996 | Hanson et al. |
| 5,550,167 A | 8/1996 | DesMarais |
| 5,563,179 A | 10/1996 | Stone et al. |

(Continued)

FOREIGN PATENT DOCUMENTS

| | | | |
|---|---|---|---|
| EP | 0 568 368 A1 | 11/1993 | ........... A61L/25/00 |
| WO | 86/03505 | 6/1986 | |
| WO | 99/61518 | 12/1999 | |
| WO | WO 00/38610 | 7/2000 | ........... A61F/13/15 |
| WO | WO 01/13843 A1 | 3/2001 | ........... A61F/13/15 |
| WO | WO 02/49565 A2 | 6/2002 | ........... A61F/13/53 |
| WO | WO 03/051412 A1 | 6/2003 | ........... A61L/15/42 |
| WO | WO 03/051417 A1 | 6/2003 | ........... A61L/15/60 |

*Primary Examiner*—Tatyana Zalukaeva
(74) *Attorney, Agent, or Firm*—Pauley Petersen & Erickson

(57) ABSTRACT

Superabsorbent polymer materials are provided including absorbent polymers having a fast vortex time, desirably about 10 seconds or less, and a stiffness index of at least about 0.7, as determined by test procedures described herein. The absorbent polymers can be modified to obtain a faster vortex time by a method including providing an absorbent polymer having a first vortex time, absorbing water with the absorbent polymer, freeze-drying the swollen absorbent polymer to remove at least a portion of the absorbed water, and obtaining a modified absorbent polymer having a second vortex time. The ratio of the first vortex time to the second vortex time is at least about 5, and desirably the modified absorbent polymer has a stiffness index of at least about 0.7.

42 Claims, 1 Drawing Sheet

U.S. PATENT DOCUMENTS

| | | | |
|---|---|---|---|
| 5,571,849 A | 11/1996 | DesMarais | |
| 5,573,994 A | 11/1996 | Kabra et al. | |
| 5,601,542 A | 2/1997 | Melius et al. | 604/368 |
| 5,612,385 A | 3/1997 | Ceaser et al. | |
| 5,632,737 A | 5/1997 | Stone et al. | |
| 5,651,862 A | 7/1997 | Anderson et al. | |
| 5,692,939 A | 12/1997 | DesMarais | |
| 5,733,272 A | 3/1998 | Brunner et al. | |
| 5,763,067 A | 6/1998 | Brüggemann et al. | |
| 5,763,499 A | 6/1998 | DesMarais | |
| 5,786,395 A | 7/1998 | Stone et al. | |
| 5,788,684 A | 8/1998 | Abuto et al. | 604/368 |
| 5,795,921 A | 8/1998 | Dyer et al. | |
| 5,843,063 A | 12/1998 | Anderson et al. | |
| 5,849,805 A | 12/1998 | Dyer | |
| 5,851,648 A | 12/1998 | Stone et al. | |
| 5,851,672 A | 12/1998 | Wang et al. | |
| 5,869,171 A | 2/1999 | Shiveley et al. | |
| 5,873,869 A | 2/1999 | Hammons et al. | |
| 5,899,893 A | 5/1999 | Dyer et al. | |
| 5,904,675 A | 5/1999 | Laux et al. | |
| 5,948,829 A | 9/1999 | Wallajapet et al. | |
| 5,985,432 A | 11/1999 | Wang et al. | |
| 5,985,434 A | 11/1999 | Qin et al. | |
| 6,019,871 A | 2/2000 | Rökman et al. | |
| 6,027,795 A | 2/2000 | Kabra et al. | |
| 6,033,769 A | 3/2000 | Brueggemann et al. | |
| 6,071,580 A | 6/2000 | Bland et al. | |
| 6,083,211 A | 7/2000 | DesMarais | |
| 6,103,358 A | 8/2000 | Brüggemann et al. | |
| 6,203,845 B1 | 3/2001 | Qin et al. | 427/2.31 |
| 6,261,679 B1 | 7/2001 | Chen et al. | |
| 6,441,266 B1 * | 8/2002 | Dyer et al. | 604/368 |
| 6,610,173 B1 | 8/2003 | Lindsay et al. | 162/109 |
| 6,646,179 B1 * | 11/2003 | Melius et al. | 604/368 |
| 2002/0040210 A1 | 4/2002 | Luccio et al. | 604/367 |
| 2002/0128618 A1 | 9/2002 | Frenz et al. | 604/368 |
| 2002/0156441 A1 * | 10/2002 | Sawyer et al. | 604/368 |
| 2003/0130640 A1 | 7/2003 | Dodge, II et al. | 604/368 |
| 2003/0139712 A1 | 7/2003 | Dodge, II et al. | 604/368 |
| 2003/0139715 A1 * | 7/2003 | Dodge et al. | 604/368 |
| 2003/0139717 A1 | 7/2003 | Qin et al. | 604/369 |

\* cited by examiner

HIGH STIFFNESS ABSORBENT POLYMERS HAVING IMPROVED ABSORBENCY RATES AND METHOD FOR MAKING THE SAME

FIELD OF INVENTION

The present invention relates to superabsorbent materials including absorbent polymers having fast absorption rates and high stiffness. The invention also relates to a method of improving the absorption rate of high stiffness absorbent polymers.

BACKGROUND OF THE INVENTION

Absorbent polymer materials, also known as superabsorbent materials, are known in the art for use in absorbent articles such as disposable diapers. The superabsorbent materials can absorb large amounts of fluid, even absorbing more than ten times its weight. Superabsorbent materials are often used in combination with additional materials, particularly fibrous materials, and absorbent article layers, such as a surge layer, which allow for rapid intake of fluids into the absorbent article. These additional materials and layers can act to temporarily hold the fluids until the superabsorbent materials can absorb the relatively large amounts of fluid. Stiff absorbent polymer superabsorbent particles can be used when the absorbent article is under pressure, such as a diaper on an infant, to help maintain an open structure in the absorbent article allowing passage of the fluid to the superabsorbent materials. Therefore it is often desirable that superabsorbent materials include an absorbent polymer having a high stiffness as well as fast absorption properties. In addition, superabsorbent materials desirably have the ability to rapidly absorb fluids from one or more insults from a diaper user.

Current commercial superabsorbent materials typically do not include absorbent polymers having the high stiffness properties as well as fast absorbency rates desired in absorbent articles. There is a need for superabsorbent materials including absorbent polymers having both a high stiffness and a fast fluid absorption rate. There is also a need for a method to modify high stiffness absorbent polymers to increase the absorption rate without unduly reducing the stiffness.

SUMMARY OF THE INVENTION

This invention relates to superabsorbent materials including high stiffness absorbent polymers that solve the above identified problems. This invention also relates to a method of modifying a high stiffness absorbent polymer to increase the absorbency rate. In one embodiment of this invention, the method includes providing an absorbent polymer having a first vortex time, absorbing water with the absorbent polymer, removing at least a portion of the absorbed water from the absorbent polymer, and obtaining a modified absorbent polymer having a second vortex time. A ratio of the first vortex time to the second vortex time is at least about 5, and the modified absorbent polymer desirably has a stiffness index of at least about 0.7.

In another embodiment of this invention, a method of modifying an absorbent polymer includes providing an absorbent polymer having a first vortex time of greater than about 10 seconds, absorbing water with the absorbent polymer, freeze-drying the swollen absorbent polymer to remove at least a portion of the absorbed water, and obtaining a modified absorbent polymer having a second vortex time of about 10 seconds or less and a stiffness index of at least about 0.7.

The method of this invention produces high stiffness absorbent polymer superabsorbent materials having improved absorbency rates. The invention provides a superabsorbent material including an absorbent polymer having a vortex time of about 10 seconds or less and a stiffness index of at least about 0.7. The absorbent polymer can be a modified absorbent polymer. In one particular embodiment, the invention provides a superabsorbent material including a freeze-dried sodium polyacrylate absorbent polymer having a stiffness index of at least about 0.7. The polyacrylate absorbent polymer has a first vortex time before freeze-drying and a second vortex time after freeze-drying. The ratio of the first vortex time to the second vortex time is at least about 5.

BRIEF DESCRIPTION OF THE DRAWINGS

These and other objects and features of this invention will be better understood from the following detailed description taken in conjunction with the drawings, wherein.

DESCRIPTION OF PREFERRED EMBODIMENTS DEFINITIONS

Figure 1:
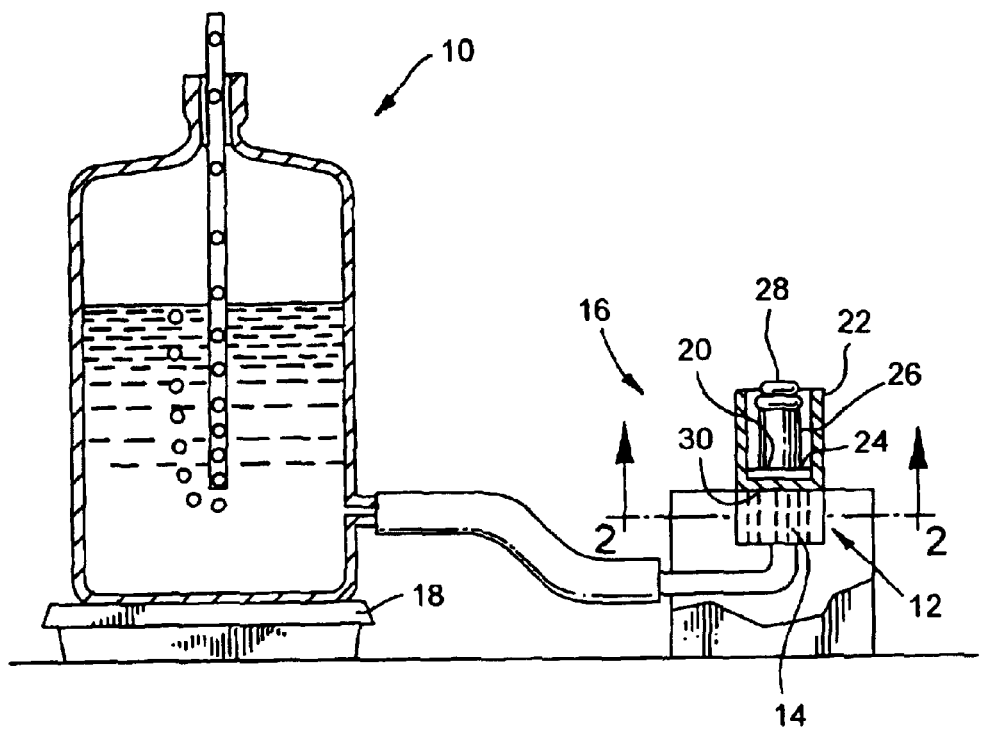
FIG. 1 is an illustration of equipment for determining the Absorbency Under Load (AUL) value of an absorbent polymer.

"Absorbent polymer" refers to an organic or inorganic polymer material capable, under the most favorable conditions, of absorbing at least about 10 times its weight, preferably at least about 30 times its weight in an aqueous solution containing 0.9 percent by weight sodium chloride. The absorbent polymers of this invention can comprise particles, fibers, and/or other structural forms. The absorbent polymers are preferably lightly crosslinked to render the materials substantially water insoluble. Crosslinking may, for example, be accomplished by irradiation or by covalent, ionic, Van der Waals, or hydrogen bonding.

"Polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the molecule. These configurations include, but are not limited to isotactic, syndiotactic and random symmetries.

"Superabsorbent material" refers to a water-swellable, water-insoluble material including an organic or inorganic absorbent polymer capable, under the most favorable conditions, of absorbing at least about 10 times its weight, preferably at least about 30 times its weight in an aqueous solution containing 0.9 percent by weight sodium chloride. Superabsorbent materials can comprise particles, fibers, and/or other structural forms. "Water-swellable, water-insoluble" refers to the ability of a material to swell to an equilibrium volume in excess water but not dissolve into the water. The water-swellable, water-insoluble material generally retains its original identity or physical structure, even in a highly expanded state during the absorption of water. Superabsorbent materials can include additional treatment materials, such as surfactants, to the absorbent polymer. For purposes of this invention, where the absorbent polymer cannot be separated from the additional treatment materials of the superabsorbent material, by means known in the art, for testing, "absorbent polymer" will include those inseparable additional treatment materials.

This invention relates to water-swellable, water insoluble superabsorbent materials including an absorbent polymer having a high stiffness and a fast absorption rate. Another aspect of this invention refers to a method to increase the absorption rate of absorbent polymers, particularly absorbent polymers having a high stiffness. As used herein, "stiffness" or "stiff" refers to the ability of the absorbent polymer to resist deformation against pressure, particularly while in a swollen state, and "high stiffness" refers to a stiffness index of at least about 0.7 as determined by test procedures described below. "Stiffness index" refers to the ratio of the absorbency under load (AUL) value of the absorbent polymer divided by the centrifuge retention capacity (CRC) value of the absorbent polymer. The absorbency under load of the absorbent polymer is determined by the Absorbency Under Load (AUL) Test described below at a load of about 0.9 pounds per square inch (6.2 kiloPascals). The centrifuge retention capacity of the absorbent polymer is determined by the Centrifuge Retention Capacity (CRC) Test also described below.

"Absorption rate" refers to the ability of the absorbent polymer to absorb an amount of liquid as a function of time. Absorption rates of the absorbent polymer herein are measured by the vortex time of the absorbent polymer. "Vortex time" refers to the amount of time in seconds required for an amount of absorbent polymer to close a vortex created by stirring an amount of 0.9 percent (%) by weight sodium chloride solution according to the Vortex Time Test described below. The vortex times described herein are obtained with an absorbent polymer particle size range of about 300 to 600 microns.

In one embodiment of this invention, a superabsorbent material includes an absorbent polymer having a vortex time of about 10 seconds or less, more suitably about 5 seconds or less, and desirably about 3 seconds or less, and a stiffness index of at least about 0.7, more suitably at least about 0.8, and desirably at least about 0.9. The superabsorbent materials of this invention can include any absorbent polymers, such as (1) the anionic polymers, such as the alkali metal and ammonium salts of poly(acrylic acid), poly(methacrylic acid), isobutylene-maleic anhydride copolymers, poly(vinyl acetic acid), poly(vinyl phosphonic acid), poly(vinyl sulfonic acid), carboxymethyl cellulose, carboxymethyl starch, carrageenan, alginic acid, polyaspartic acid, polyglutamic acid, and combinations and copolymers thereof, (2) the cationic polymers, such as salts of poly(vinyl amine), poly (ethylene imine), poly(amino propanol vinyl ether), poly (allyl amine), poly(quaternary ammonium), poly(diallyl dimethyl ammonium hydroxide), polyasparagins, polyglutamines, polylysines, polyarginines, and combinations and copolymers thereof, (3) the mixture of anionic and cationic superabsorbent polymers, such as any combination of at least each one from Groups (1) and (2); (4) the mixture of acidic and basic polymers, such as acidic polymers from non-neutralized anionic superabsorbent polymers of Group (1) and basic polymers from non-neutralized cationic superabsorbent polymers of Group (2). In one embodiment of this invention the absorbent polymer includes one of sodium polyacrylate, polyvinyl amine salt, polyacrylic acid, polyvinyl amine, and combinations and derivatives thereof.

The high stiffness and fast absorption rate absorbent polymers of this invention are useful in various types of absorbent composite structures for various absorbent articles. The absorbent article can include an absorbent composite that includes a superabsorbent material comprising an absorbent polymer having a vortex time of about 10 seconds or less and a stiffness index of at least about 0.7 intermixed with water-insoluble fibers. The absorbent composites of this invention suitably include about 5 to 95 percent by weight superabsorbent material. Using a superabsorbent material including an absorbent polymer having a high stiffness in an absorbent composite typically provides a more open porous composite structure, as the superabsorbent material does not deform as much during the swelling process (as compared to low stiffness superabsorbent materials). The absorbent composites having the high stiffness and fast absorption rate absorbent polymers of this invention may be used alone or in combination with other absorbent or fluid handling layers, such as a surge layer. The superabsorbent materials of this invention including high stiffness and fast absorption rate absorbent polymers are useful in absorbent articles such as diapers, training pants, swim wear, adult incontinence articles, feminine care products, underarm pads, bed matting, tissues, wipes, and medical absorbent products.

It has been discovered that current commercial high stiffness absorbent polymers not having a desired vortex time can be modified to obtain an improved, more desirable vortex time. In one embodiment of this invention, a high stiffness absorbent polymer can be modified to increase the absorption rate. The method of modifying the high stiffness absorbent polymer includes providing an absorbent polymer having a first vortex time, absorbing an amount of fluid, desirably distilled water, with the absorbent polymer, removing at least a portion of the absorbed water from the absorbent polymer, and obtaining a modified absorbent polymer having a second vortex time and a stiffness index of at least about 0.7. The removal of the water desirably is done so as to allow the absorbent polymer to retain the swollen structure. Not intending to be bound by theory, the absorption of the water causes the absorbent polymer to swell and create a more open, porous absorbent polymer. When the water is removed from the swollen absorbent polymer in such a way so as to allow the absorbent polymer to retain the more open, porous structure obtained while swollen, the absorption rate of the absorbent polymer will increase. Upon contact with fluid such as water or urine, the modified absorbent polymer more quickly absorbs the fluid due to the more open, porous structure.

Modifying an absorbent polymer, and particularly a high stiffness absorbent polymer, according to the method of this invention provides a decreased, or faster, vortex time. By the method of this invention, the vortex time of the absorbent polymer is decreased so that a ratio of the first vortex time to a second vortex time of the modified absorbent polymer is at least about 5. More suitably the ratio of the first vortex time to the second vortex time is at least about 10, and desirably the ratio of the first vortex time to the second vortex time is at least about 20. The method can be used to modify absorbent polymers having any stiffness index, but is particularly desirable for modifying high stiffness absorbent polymers to obtain a modified absorbent polymer having a stiffness index of at least about 0.7. In one embodiment of this invention, the modified absorbent polymer has a stiffness index of at least about 0.7, more suitably at least about 0.8, and desirably at least about 0.9, and desirably a ratio of the first vortex time to the second vortex time of at least about 5.

As described above, the method of modifying an absorbent polymer of this invention includes absorbing an amount of water with the absorbent polymer and removing at least a portion of the absorbed water. The amount of water absorbed determines the swelling level and the final structure of the modified absorbent polymer. Thus, the amount of water absorbed and/or the larger the portion of the absorbed water removed will affect the structure of the modified absorbent polymer and the resulting second vortex time. Therefore, any amount of water can be absorbed by the absorbent polymer according to the method of this invention, although absorbing more water, thereby obtaining a higher swelling level, generally results in a faster second vortex time and a larger resulting ratio of the first vortex time to the second vortex time. However, as is discussed below, absorbing water to obtain higher swelling levels can cause a decrease in stiffness. In one embodiment of this invention, the absorbent polymer absorbs water to obtain an absorbent polymer swelling level of at least about 5 grams water/gram absorbent polymer, more suitably at least about 10 grams water/gram absorbent polymer, and desirably at least about 20 grams water/gram absorbent polymer. Desirably, substantially all the absorbed water is removed from the absorbent polymer, although removal of only a portion of the absorbed water can provide the faster second vortex time.

The method of this invention can be used to decrease the vortex time of a high stiffness absorbent polymer without significantly affecting the stiffness index. There are two interrelated controllable factors that have been identified that allow the absorbent polymer to be modified according to the methods of this invention without a significant reduction in stiffness. The two factors are: 1) the degree of swelling of the absorbent polymer; and 2) the particle size of the high stiffness absorbent polymers used in the modification methods of this invention.

Typical commercial superabsorbent particles include absorbent polymers that are heterogeneously crosslinked. Heterogeneous crosslinking, also referred to as surface crosslinking, results in an absorbent polymer particle having more absorbent polymer crosslinking at a particle surface than toward a center of the particle. Without intending to be bound by theory, it is believed that as the superabsorbent particle swells in the presence of a liquid, the crosslinked surface will expand and cause some of the surface polymer crosslinks to "break," thereby exposing the less-crosslinked, and therefore lower stiffness, center of the absorbent polymer particle. The amount and chemical nature of the crosslinking affects the stiffness index of an absorbent polymer particle. Therefore, a higher absorbent polymer particle swelling level can result in more exposure of the lesser crosslinked center, and a decrease in the overall stiffness index of the particle.

Particle size selection for high stiffness absorbent polymers also plays a role in maintaining the desired stiffness index of the absorbent polymers being modified according to the methods of this invention. Absorbent polymer particle size is typically important in the construction of absorbent articles. Absorbent composites are often densified before being placed in an absorbent article. The densification process typically involves pressing the absorbent composite. The densification process can break apart absorbent polymer particles, particularly larger particles. Breaking the absorbent polymer particles into smaller particles during densification can lower the stiffness index of the absorbent polymer particles due to the resulting lower amounts of surface crosslinking in the broken, smaller particles. The testing methods of this invention described below use a particle size of about 300 to 600 micrometers. This range represents a relatively smaller particle that is more likely to be used in absorbent composites for commercial absorbent articles.

The modification methods of this invention swell an absorbent polymer to a swollen size larger than the original, pre-swollen size. By using smaller size absorbent polymer particles in the modification methods of this invention, the stiffness index of a high stiffness absorbent polymer can be maintained, particularly when higher swelling levels of the high stiffness absorbent particle are used during modification. The smaller, pre-swelling particle size allows for modification through swelling and removal of the water without requiring post-modification mechanical reduction, such as grinding, of the particle size for testing, or causing size reduction during the typical densification process during use in absorbent articles.

Obtaining a high stiffness modified absorbent polymer material having a fast absorption rate according to methods of this invention is dependent on the pre-swelling particle size as well as the swelling level obtained during the modification method. In one embodiment of the method of this invention, the absorbent polymer includes particles having a pre-modification particle size of about 850 micrometers or less, more suitably about 600 micrometers or less, desirably about 300 micrometers or less, and more desirably about 150 micrometers or less, and absorbs water to obtain an absorbent polymer swelling level of at least about 5 grams water/gram absorbent polymer. At higher swelling levels, smaller particle size diameters are desired. In another embodiment of the method of this invention, the absorbent polymer includes particles having a pre-modification particle size of about 600 micrometers or less, suitably about 300 micrometers or less, and desirably 150 micrometers or less, and absorbs water to obtain an absorbent polymer swelling level of at least about 10 grams water/gram absorbent polymer. In yet another embodiment of the method of this invention, the absorbent polymer includes particles having a pre-modification particle size of about 300 micrometers or less, and desirably about 150 micrometers or less, and absorbs water to obtain an absorbent polymer swelling level of at least about 20 grams water/gram absorbent polymer.

The absorbed water can be removed by any process that removes at least a portion of the water yet allows the absorbent polymer to retain the swollen structure. "Swollen" refers to the form of the absorbent polymer upon absorption of fluid, as the absorbent polymer will swell, or become larger, due to the absorbed fluid. One process for removal of at least a portion of the water is freeze-drying the swollen absorbent polymer. Freeze-drying the absorbent polymer is accomplished by absorbing an amount of fluid, desirably distilled water, into the absorbent polymer. Mixing the absorbent polymer and the water in a mixer can provide similar swelling among the absorbent polymer particles. The swollen absorbent polymer is placed into a pan to form a uniform thin layer. The swollen absorbent polymer is frozen and the removal of the frozen water is preferably done by vacuum sublimation. Placing the pan in a freeze-dryer, such as a VirTis Genesis freeze-dryer, available from The VirTis Inc. of Gardiner, N.Y., is one way of freezing and vacuum sublimating the water.

Vacuum conditions are desirably about 500 millitorrs or less, about 300 millitorrs or less, about 200 millitorrs or less, or about 100 millitorrs or less. In general, good vacuum can be achieved by either a good quality vacuum pump or a lower condenser temperature, which captures more water vapor. Because sublimation is endothermic, the temperature of the frozen absorbent polymer is reduced as water is sublimated under vacuum. This means that the frozen absorbent polymer will be even colder and therefore it becomes more difficult to release water molecules. In order to compensate such energy loss, the freeze dryer should be equipped with a heater which provides just enough heat to compensate the energy loss to maintain temperature at a predetermined level. Suitable freeze-drying parameters include a shelf temperature of about −50° C. or less, a condenser temperature of about −70° C. or less, and a vacuum of about 100 millitorrs or less.

In one embodiment of this invention, a method of modifying an absorbent polymer includes providing an absorbent polymer having a first vortex time of greater than about 10 seconds, absorbing water with the absorbent polymer, freeze-drying the swollen absorbent polymer to remove at least a portion of the absorbed water, and obtaining a modified absorbent polymer having a second vortex time of about 10 seconds or less, more suitably about 5 seconds or less, and desirably about 3 seconds or less. The modified absorbent polymer suitably has a stiffness index of at least about 0.7 after freeze-drying, desirably at least about 0.8, and more desirably at least about 0.9.

The absorbent polymer suitably absorbs water to obtain an absorbent polymer swelling level of at least about 5 grams water/gram absorbent polymer, more suitably at least about 10 grams water/gram absorbent polymer, and desirably at least about 20 grams water/gram absorbent polymer, and having an appropriate particle size for the particular swelling level. Desirably substantially all of the absorbed water is removed by freeze-drying, although the faster second vortex time of the high stiffness modified absorbent polymer can be obtained by removal of at least a portion of the water.

In one embodiment of this invention, a superabsorbent material includes a freeze-dried sodium polyacrylate polymer having a stiffness index of at least about 0.7, more suitably at least about 0.8, and desirably at least about 0.9. The polyacrylate polymer has a first vortex time before freeze-drying and a second vortex time after freeze-drying wherein the ratio of the first vortex time to the second vortex time is at least about 5, more suitable at least about 10, and desirably at least about 20.

Absorbency Under Load (AUL) Test

The Absorbency Under Load (AUL) test is a measure of the ability of an absorbent polymer to absorb a liquid while the absorbent polymer is under a restraining load. The test may best be understood by reference to FIGS. 1 and 2. Referring to FIG. 1, a demand absorbency tester (DAT) 10 is used, which is similar to a GATS (gravimetric absorbency test system), available from M/K Systems, Danners, Mass., as well as a system described by Lichstein in pages 129–142 of the INDA Technological Symposium Proceedings, March 1974.

Figure 2:
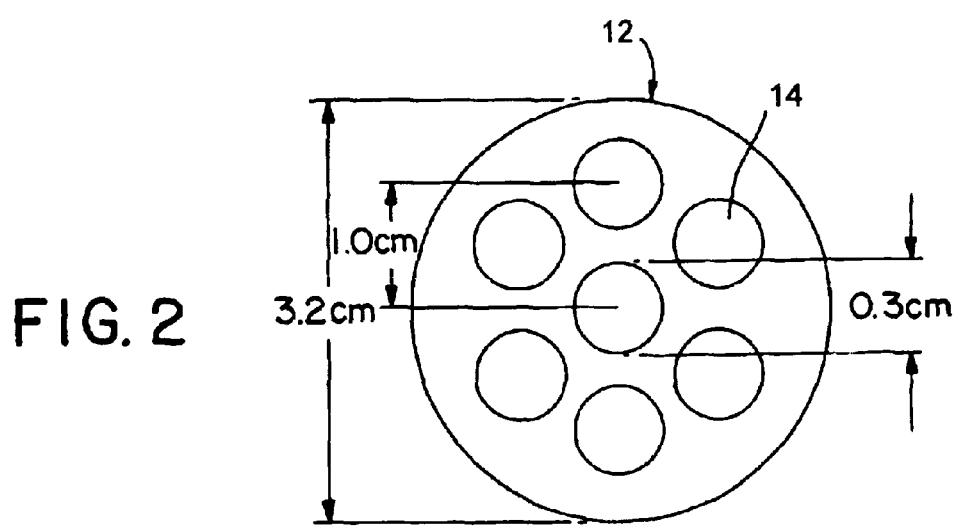
FIG. 2 is a cross-sectional view of the porous plate taken along line 2—2 of FIG. 1.

A porous plate 12 is used having ports 14 confined within the 2.5 centimeters diameter covered, in use, by the Absorbency Under Load apparatus 16. FIG. 2 shows a cross-sectional view of porous plate 12. The porous plate 12 has a diameter of 3.2 centimeters with 7 ports (holes) 14 each with diameter of 0.30 centimeters. The porous plate 12 has one hole 14 in the center and the holes are spaced such that the distance from the center of one hole to another adjacent to it is 1.0 centimeter. An electrobalance 18 is used to measure the flow of the test fluid (an aqueous solution containing 0.9 percent by weight sodium chloride) into the absorbent polymer 20.

The AUL apparatus 16 used to contain the absorbent polymer may be made from 1 inch (2.54 centimeters), inside diameter, thermoplastic tubing 22 machined-out slightly to be sure of concentricity. A U.S. Standard #100 mesh (0.149 millimeter openings) stainless steel wire cloth 24 is adhesively attached to the bottom of tubing 22. Alternatively, the steel wire cloth 24 may be heated in a flame until red hot, after which the tubing 22 is held onto the cloth until cooled. Care should be taken to maintain a flat, smooth bottom and not distort the inside of the tubing 22. A 4.4 gram piston 26 may be made from 1 inch (2.54 centimeters) solid material (e.g., Plexiglas) and machined to closely fit, without binding, in the tubing 22. A 317 gram weight 28 is used to provide 62,000 dynes per square centimeter (about 0.9 pounds per square inch (psi)) restraining load on the superabsorbent material. For the purpose of the present invention, the pressure applied during the AUL test is 0.9 pounds per square inch (6.2 kiloPascals).

Desirably, about 0.160 grams of absorbent polymer is used. The sample includes absorbent polymer particles, which are pre-screened through U.S. standard #30 mesh screen (0.595 millimeter openings) and retained on U.S. standard #50 mesh screen (0.297 millimeter openings). The absorbent polymer, therefore, has a particle size of about 300 to 600 microns. The particles may be pre-screened by hand or automatically pre-screened with, for example, a Ro-Tap Mechanical Sieve Shaker Model B available from W. S. Tyler, Inc., Mentor, Ohio.

The desired amount of absorbent polymer 20 (0.160 grams) is weighed onto weigh paper and placed on the wire cloth 24 at the bottom of the tubing 22. The tubing 22 is shaken to level the absorbent polymer on the wire cloth 24. Care is taken to be sure no absorbent polymer is clinging to the wall of the tubing 22. The piston 26 and weight 28 are carefully placed on the absorbent polymer to be tested. The test is initiated by placing a 3 centimeter diameter glass filter paper 30 (Whatman filter paper Grade GF/A, available from Whatman International Ltd., Maidstone, England) onto the plate 12 (the paper is sized to be larger than the internal diameter and smaller than the outside diameter of the tubing 22) to ensure good contact, while eliminating evaporation over the ports 14 of the demand absorbency tester 10 and then allowing saturation to occur. The device is started by placing the apparatus 16 on the glass filter paper 30 and allowing saturation to occur. The amount of fluid picked up is monitored as a function of time either directly by hand, with a strip chart recorder, or directly into a data acquisition or personal computer system.

The amount of fluid pick-up measured after 60 minutes is the AUL value and is reported in grams of test liquid absorbed per gram of absorbent polymer as determined before starting the test procedure. A check can be made to ensure the accuracy of the test. The apparatus 16 can be weighed before and after the test with a difference in weight equaling the fluid pick-up.

Centrifuge Retention Capacity Test

As used herein, the centrifuge retention capacity (CRC) is a measure of the absorbent capacity of the absorbent polymer after being subjected to centrifugation under controlled conditions. The absorbent polymer sample to be tested is taken from absorbent polymer which is prescreened through a U.S. standard #30 mesh screen (0.595 millimeter openings) and retained on a U.S. standard #50 mesh screen (0.297 millimeter openings) to obtain a particle size of between 300 and 600 microns. The CRC can be measured by placing 0.200 grams of the sample material to be tested (moisture content of less than 5 weight percent) into a water-permeable bag which will contain the sample while allowing the test solution (0.9 percent by weight sodium chloride solution) to be freely absorbed by the sample. A heat-sealable tea bag material (grade 542, commercially available from Kimberly-Clark Corporation, Neenah, Wis.) works well for most applications. The bag is formed by folding a 12.7 centimeter by 7.62 centimeter sample of the bag material in half and heat sealing two of the open edges to form a 6.35 by 7.62 centimeter rectangular pouch. The heat seals should be about 0.635 centimeters inside the edge of the material. After the sample is placed in the pouch, the remaining open edge of the pouch is also heat-sealed. Empty bags are also made to be tested with the sample bags as controls. Three sample bags are tested for each superabsorbent material.

The sealed bags are placed between two Teflon coated fiberglass screens having 0.635 centimeter openings (Taconic Plastics, Inc., Petersburg, N.Y.) and submerged in a pan of 0.9 percent by weight sodium chloride solution at about 23° C., making sure that the screens are held down until the bags are completely wetted. After wetting, the samples remain in the solution for 30 minutes, at which time they are removed from the solution and temporarily laid on a nonabsorbent flat surface. The wet bags are then placed into the basket of a suitable centrifuge capable of subjecting the samples to a force equivalent to 300 times the acceleration due to gravity. A suitable centrifuge is a Heraeus Instruments Labofuge 400, having a water collection basket, digital rotations per minute (rpm) gauge, and machined drainage basket adapted to hold and drain the samples. The samples must be placed in opposing positions within the centrifuge to balance the basket when spinning. The bags are centrifuged at a target of 1600 rotations per minute, but within the range of 1500–1900 rotations per minute, for 3 minutes (target force of 300 times the acceleration due to gravity). The bags are removed and weighed, with the empty bags (controls) being weighed first, followed by the bags containing the superabsorbent material. The amount of fluid absorbed and retained by the absorbent polymer, taking into account the fluid retained by the bag material alone, is the Centrifuge Retention Capacity of the superabsorbent material, expressed as grams of fluid per gram of material. This calculation is done by the following equation:

$$CRC = \frac{(W_s - W_e - W_d)}{W_d}$$

where "CRC" is the Centrifuge Retention Capacity of the sample (grams/gram), "$W_s$" is the after centrifuged mass of the teabag and the sample (grams), "$W_e$" is the average after centrifuged mass of the empty teabag (grams), and "$W_d$" is the dry mass of the sample (grams). The CRC measurements for each of three replicates are averaged to provide the CRC value of the material.

Vortex Time Test

The Vortex Time Test measures the amount of time in seconds required for a predetermined mass of an absorbent polymer to close a vortex created by stirring 50 milliliters of 0.9 percent by weight sodium chloride solution at 600 revolutions per minute on a magnetic stir plate. The time it takes for the vortex to close is an indication of the free swell absorbing rate of the absorbent polymer. As differences in centrifuge retention capacity (which can be dependent on particle size) between absorbent polymers can affect the vortex time, the vortex time test can be compensated for better comparison of various absorbent polymers by adjusting the amount of absorbent polymer added to the 50 milliliter sodium chloride solution as compared to a standard conventional absorbent polymers.

The amount of absorbent polymer to be used in the vortex time test is determined by comparison of the centrifuge retention capacity of the new sample against a conventional absorbent polymer superabsorbent material, such as FAVOR® 880, available from Stockhausen, Inc., Greensboro, N.C., which has a centrifuge retention capacity value of 33.6 grams/gram. For determining the vortex time of FAVOR® 880, 2.0 grams of FAVOR® 880 are added to 50 milliliters of 0.9 weight percent sodium chloride solution. The amount of a different absorbent polymer to be used in the vortex time test can be determined by the following formula.

$$C = \frac{2.0 \text{ grams} \times A}{B}$$

Where "A" is the centrifuge retention capacity of the standard superabsorbent absorbent polymer (FAVOR® 880), or 33.6 grams/gram, "B" is the centrifuge retention capacity of the second superabsorbent material, and "C" is the amount of the second superabsorbent material to be used in the vortex time test.

The vortex time test is preferably done at standard room atmosphere conditions, where the temperature is 23° C. ±1° C. and relative humidity is 50 percent ±2 percent. The vortex time test is done by measure 50 milliliters (±0.01 milliliter) of 0.9 percent by weight sodium chloride solution into the 100 milliliter beaker. Place a 7.9 millimeters×32 millimeters TEFLON® covered magnetic stir bar without rings (such as that commercially available from Baxter Diagnostics, under the trade designation S/P® brand single pack round stirring bars with removable pivot ring) into the beaker. Program a magnetic stir plate (such as that commercially available from PMC Industries, under the trade designation DATA-PLATE® Model #721) to 600 revolutions per minute. Place the beaker on the center of the magnetic stir plate such that the magnetic stir bar is activated. The bottom of the vortex should be near the top of the stir bar. The absorbent polymer is pre-screened through a U.S. standard #30 mesh screen (0.595 millimeter openings) and retained on a U.S. standard #50 mesh screen (0.297 millimeter openings). The absorbent polymer, therefore, has a particle size of between about 300 and 600 microns. Weigh out the required mass of the absorbent polymer to be tested on weighing paper. While the sodium chloride solution is being stirred, quickly pour the absorbent polymer to be tested into the saline solution and start a stopwatch. The absorbent polymer to be tested should be added to the saline solution between the center of the vortex and the side of the beaker. Stop the stopwatch when the surface of the saline solution becomes flat and record the time. The time, recorded in seconds, is reported as the vortex time.

EXAMPLES

The stiffness index and the vortex time of several commercial absorbent polymer superabsorbent materials were tested according to the tests described above. The results of the testing are reported in Table 1. The unmodified superabsorbent materials tested were HYSORB® 7050, available from BASF, Portsmouth, Va., DRYTECH® 2035, available from Dow Chemical Company, Midland, Mich., and FAVOR® 880 available from Stockhausen, Inc., Greensboro, N.C.

TABLE 1

| Superabsorbent Material | Stiffness Index | Vortex Time (seconds) |
|---|---|---|
| HYSORB ® 7050 | 0.73 | 72 |
| DRYTECH ® 2035 | 0.48 | 87 |
| FAVOR ® 880 | 0.65 | 98 |

To demonstrate the method of this invention and how the method can be used to decrease the vortex time of an absorbent polymer, eighteen absorbent polymer superabsorbent samples were modified and, along with five unmodified control samples, tested according to the test methods described above. Samples 1–5 (lot no. X101320), 6–9 (no lot number available, but absorbent polymer material properties were within the specifications of manufacturer), and 10–15 (lot no. X109820) included control FAVOR® 9543 and modified FAVOR® 9543, available from Stockhausen, Inc., Greensboro, N.C. Samples 16–20 (lot no. X807519) included a control FAVOR® 880 and modified FAVOR® 880. Samples 21–23 included a control DRYTECH® 2035 and modified DRYTECH® 2035 (lot no. PK28011Y55).

Samples 1, 6, 10, 16, and 21, were tested as controls of the appropriate material without any modification. Eighteen samples, Samples 2–5, 7–9, 11–15, 17–20, and 22–23, of known absorbent polymer superabsorbent materials were modified by freeze-drying according to the following method. For each of Samples 2–5, 7–9, 11–15, 17–20, and 22–23, an appropriate amount of distilled water, as summarized in Table 2, was used to obtain a desired swelling level. The respective amount of distilled water was added into a one gallon HOBART® mixer (Model N50, manufactured by Hobart Canada, Ontario, Canada). The desired mass of the absorbent polymer superabsorbent particles having the respective particle size were added into the mixer while the stirrer was on. After stirring for about 2 minutes, the swollen absorbent polymer superabsorbent particles were discharged into a pan (10 inches by 20 inches or 25.4 centimeters by 50.8 centimeters) to form a uniform thin layer. The pan was placed into a VirTis Genesis freeze dryer (Model 25 EL) available from The VirTis Inc, of Gardiner, N.Y. The superabsorbent material was freeze-dried in the freeze dryer at a shelf temperature of less than −50° C., a condenser temperature of less than −70° C., and a vacuum of less than 100 millitorrs. The particle size, before swelling, of the Samples as well as the preparation specifics are summarized in Table 2. As the stiffness index and vortex time of each Sample is determined using particles having a size of about 300 micrometers to 600 micrometers, smaller pre-swelling particle sizes were utilized for Samples with higher swelling levels to obtain swollen Sample particles within the desired range for testing. However, Samples 3–5 had to be ground after swelling to obtain particles within this size range using an OSTERIZER® 12-speed blender, available from Sunbeam, Inc., at high speed for 30 seconds.

TABLE 2

| Sample | Particle size before swelling (microns) | Water amount (g) | SAM amount (g) | Swelling Level (g/g) |
|---|---|---|---|---|
| 1 | N/A | N/A | N/A | N/A |
| 2 | <850 | 1000 | 200 | 5 |
| 3 | <850 | 1000 | 100 | 10 |
| 4 | <600 | 1500 | 75 | 20 |
| 5 | <300 | 3000 | 75 | 40 |
| 6 | N/A | N/A | N/A | N/A |
| 7 | <850 | 100 | 100 | 1 |
| 8 | <850 | 200 | 100 | 2 |
| 9 | <850 | 500 | 100 | 5 |
| 10 | N/A | N/A | N/A | N/A |
| 11 | 150–300 | 200 | 40 | 5 |
| 12 | 150–300 | 240 | 30 | 8 |
| 13 | 150–300 | 300 | 30 | 10 |
| 14 | <150 | 600 | 30 | 20 |
| 15 | <150 | 2000 | 40 | 50 |
| 16 | N/A | N/A | N/A | N/A |
| 17 | <850 | 60 | 30 | 2 |
| 18 | 150–300 | 150 | 30 | 5 |
| 19 | 150–300 | 240 | 30 | 8 |
| 20 | <150 | 1200 | 30 | 40 |
| 21 | N/A | N/A | N/A | N/A |
| 22 | <850 | 60 | 30 | 2 |
| 23 | <150 | 1200 | 30 | 40 |

Each of Samples 1–23 were tested according to the Absorbency Under Load (AUL) test, the Centifuge Retention Capacity (CRC) Test, and the Vortex Time Test, as describe above. The test results as well as the stiffness index and the ratio of the first, pre-modification, vortex time to the second, post-modification, vortex time for each of Samples 1–23 are summarized in Table 3.

TABLE 3

| Samples | CRC (g/g) | AUL (g/g) | Pre-modification Vortex Time (seconds) | Post-modification Vortex Time (seconds) | Vortex Time Ratio | Stiffness Index |
|---|---|---|---|---|---|---|
| 1 (Control) | 22.2 | 18.8 | 48.9 | N/A | N/A | 0.85 |
| 2 | 20.2 | 17.3 | 48.9 | 8.8 | 5.6 | 0.85 |
| 3 | 20.3 | 11.3 | 48.9 | 4.8 | 10.2 | 0.56 |
| 4 | 19.1 | 9.15 | 48.9 | 3.6 | 13.6 | 0.49 |
| 5 | 17.9 | 11.5 | 48.9 | <1 | >48.9 | 0.64 |
| 6 (Control) | 23.2 | 21.4 | 83.0 | N/A | N/A | 0.92 |
| 7 | 20.6 | 18.6 | 83.0 | 46.7 | 1.8 | 0.90 |
| 8 | 20.3 | 18.9 | 83.0 | 28.5 | 2.9 | 0.93 |
| 9 | 20.2 | 17.7 | 83.0 | 16.7 | 5.0 | 0.88 |
| 10 (Control) | 23.1 | 20.1 | 76.5 | N/A | N/A | 0.87 |
| 11 | 18.7 | 18.3 | 76.5 | 8.57 | 8.9 | 0.98 |
| 12 | 18.6 | 17.6 | 76.5 | 6.74 | 11.4 | 0.95 |
| 13 | 18.4 | 16.9 | 76.5 | 5.62 | 13.6 | 0.92 |
| 14 | 15.8 | 14.6 | 76.5 | 2.45 | 31.2 | 0.92 |
| 15 | 17.0 | 14.5 | 76.5 | 1.64 | 46.6 | 0.85 |
| 16 (Control) | 33.8 | 1.9 | 98.2 | N/A | N/A | 0.65 |
| 17 | 29.9 | 19.3 | 98.2 | 34.1 | 2.9 | 0.64 |
| 18 | 25.7 | 17.2 | 98.2 | 8.7 | 11.3 | 0.66 |
| 19 | 25.9 | 15.9 | 98.2 | 6.8 | 14.4 | 0.61 |
| 20 | 21.8 | 9.2 | 98.2 | 2.2 | 44.6 | 0.42 |
| 21 (Control) | 28.5 | 13.7 | 86.7 | N/A | N/A | 0.48 |
| 22 | 25.1 | 11.0 | 86.7 | 18.1 | 4.8 | 0.43 |
| 23 | 26.1 | 6.5 | 86.7 | 2.0 | 43.4 | 0.24 |

As seen in Table 3, modifying the commercial absorbent polymer superabsorbent materials according to this invention resulted in decreased vortex times. Modified Samples, 2, 9, and 11–15 have the desired stiffness index and ratio of the first, pre-modification vortex time to the second, post-modification vortex time of the modified absorbent polymers of this invention. Samples 3–5 demonstrate the relationship between particle size and swelling level and their effect on stiffness index. Samples 3–5 had to be ground down due to the large particle size that results from higher swelling levels (10 g/g and higher) and higher pre-swelling particle sizes. The grinding of Samples 3–5 resulted in a drastic decrease in the stiffness index of these samples. For comparison, Sample 2, which was not ground, maintained the same stiffness index as the control Sample 1. Sample 15 had a smaller, pre-swelling particle size (<150) and a higher swelling level (50 g/g) than Sample 5, and Sample 15 did not require grinding to obtain particles having a size of 300 to 600 micrometers. Therefore, Sample 15 did not have a significant reduction in stiffness index as compared to its control (Sample 10). Although from different lots, Samples 5 and 15 were both FAVOR® 9543 particles.

Also, the results in Table 3 show a trend that the higher the swelling level the more stiffness index may be compromised. For instance, Sample 16, the control for FAVOR® 880, had a stiffness index of 0.65 while Sample 20, the FAVOR® 880 at a swelling level of 40 g/g, had a stiffness index of 0.42. In Samples 6–9 and 11–15, which are higher stiffness superabsorbent particles than Samples 16–20, there is a gradual decrease in stiffness index as the swelling level increases.

The results in Table 3 demonstrate that the methods of this invention can be used to decrease the vortex time of absorbent polymers while maintaining a desirable stiffness index. The results also demonstrate that decreasing vortex time while maintaining a desirable high stiffness index is dependent on selection of proper pre-swelling particle size coupled with an appropriate swelling level. Modifying the high stiffness absorbent polymer superabsorbent material FAVOR® 9543 according to the freeze-drying method of this invention, using a proper particle size and swelling level, resulted in a second, faster post-modification vortex time, while maintaining a desirable stiffness index. The stiffness index of the absorbent polymers is not substantially affected by freeze-drying unless the superabsorbent materials are ground, or otherwise mechanically altered, or the swelling level is relatively high. Thus the methods of this invention for modifying an absorbent polymer can be used to provide a superabsorbent material including an absorbent polymer with the desired high stiffness as well as a fast vortex time.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. A superabsorbent material, comprising:
   an absorbent polymer having a vortex time of about 10 seconds or less and a stiffness index of at least about 0.7.

2. The superabsorbent material of claim 1, wherein the absorbent polymer has a vortex time of about 5 seconds or less.

3. The superabsorbent material of claim 2, wherein the absorbent polymer has a vortex time of about 3 seconds or less.

4. The superabsorbent material of claim 1, wherein the absorbent polymer has a stiffness index of at least about 0.8.

5. The superabsorbent material of claim 4, wherein the absorbent polymer has a vortex time of about 5 seconds or less.

6. The superabsorbent material of claim 5, wherein the absorbent polymer has a vortex time of about 3 seconds or less.

7. The superabsorbent material of claim 1, wherein the absorbent polymer has a stiffness index of at least about 0.9.

8. The superabsorbent material of claim 7, wherein the absorbent polymer has a vortex time of about 5 seconds or less.

9. The superabsorbent material of claim 8, wherein the absorbent polymer has a vortex time of about 3 seconds or less.

10. The superabsorbent material of claim 1, wherein the absorbent polymer is a modified absorbent polymer, and the absorbent polymer has a first vortex time greater than about 10 seconds before modification and a second vortex time of about 10 seconds or less after modification.

11. The superabsorbent material of claim 10, wherein the modified absorbent polymer is a freeze-dried absorbent polymer.

12. The superabsorbent material of claim 1, wherein the absorbent polymer includes a polymer selected from the group including an anionic polymer, a cationic polymer, an acidic polymer, a basic polymer, and combinations thereof.

13. The superabsorbent material of claim 12, wherein the absorbent polymer is selected from the group including sodium polyacrylate, polyvinyl amine salt, polyacrylic acid, polyvinyl amine, and combinations thereof.

14. The superabsorbent material of claim 1, wherein the absorbent polymer is a modified absorbent polymer, the absorbent polymer having a first vortex time before modifying and a second vortex time after modifying, wherein a ratio of the first vortex time to the second vortex time is at least about 5.

15. A method for forming the modified absorbent polymer of the superabsorbent material of claim 14, the method comprising:
   providing an absorbent polymer having the first vortex time;
   absorbing water with the absorbent polymer;
   removing at least a portion of the absorbed water from the absorbent polymer; and
   obtaining the modified absorbent polymer having the second vortex time.

16. The method of claim 15, further comprising absorbing water to obtain an absorbent polymer swelling level of at least about 5 grams water/gram absorbent polymer.

17. The method of claim 16, wherein the absorbent polymer includes a particle size of about 850 micrometers or less before absorbing water.

18. The method of claim 16, further comprising absorbing water to obtain an absorbent polymer swelling level of at least about 10 grams water/gram absorbent polymer.

19. The method of claim 18, wherein the absorbent polymer includes a particle size of about 600 micrometers or less before absorbing water.

20. The method of claim 18, further comprising absorbing water to obtain an absorbent polymer swelling level of at least about 20 grams water/gram absorbent polymer.

21. The method of claim 15, wherein the ratio of the first vortex time to the second vortex time is at least about 10.

22. The method of claim 21, wherein the ratio of the first vortex time to the second vortex time is at least about 20.

23. The method of claim 15, wherein the modified absorbent polymer has a stiffness index of at least about 0.8.

24. The method of claim 23, wherein the modified absorbent polymer has a stiffness index of at least about 0.9.

25. The method of claim 15, wherein the portion of the water is removed by freeze-drying.

26. The superabsorbent material of claim 14, wherein the modified absorbent polymer is a freeze-dried absorbent polymer, the freeze-dried absorbent polymer having the first vortex time before freeze-drying and the second vortex time after freeze-drying.

27. The superabsorbent material of claim 26 wherein the freeze-dried absorbent polymer comprises sodium polyacrylate.

28. A method for forming the modified absorbent polymer of the superabsorbent material of claim 10, the method comprising:
providing an absorbent polymer having the first vortex time of greater than about 10 seconds;
absorbing water with the absorbent polymer to obtain a swollen absorbent polymer;
freeze-drying the swollen absorbent polymer to remove at least a portion of the absorbed water; and
obtaining the modified absorbent polymer having the second vortex time of about 10 seconds or less and the stiffness index of at least about 0.7.

29. The method of claim 28, further comprising absorbing water to obtain an absorbent polymer swelling level of at least about 5 grams water/gram absorbent polymer.

30. The method of claim 28, wherein the modified absorbent polymer has a second vortex time of about 5 seconds or less.

31. The method of claim 30, wherein the modified absorbent polymer has a second vortex time of about 3 seconds or less.

32. The method of claim 28, wherein the modified absorbent polymer has a stiffness index of at least about 0.8.

33. The method of claim 32, wherein the modified absorbent polymer has a stiffness index of at least about 0.9.

34. The superabsorbent material of claim 27, wherein the absorbent polymer has a stiffness index of at least about 0.8.

35. The superabsorbent material of claim 34, wherein the absorbent polymer has a stiffness index of at least about 0.9.

36. The superabsorbent material of claim 27, wherein the ratio of the first vortex time to the second vortex time is at least about 10.

37. The superabsorbent material of claim 36, wherein the absorbent polymer has a stiffness index of at least about 0.8.

38. The superabsorbent material of claim 37, wherein the absorbent polymer has a stiffness index of at least about 0.9.

39. An absorbent composite comprising about 5 percent to 95 percent by weight of the superabsorbent material of claim 27.

40. An absorbent article comprising the superabsorbent material of claim 27.

41. An absorbent composite comprising about 5 percent to 95 percent by weight of the superabsorbent material of claim 1.

42. An absorbent article comprising the superabsorbent material of claim 1.

* * * * *